(12) United States Patent
Ryan

(10) Patent No.: US 7,338,494 B2
(45) Date of Patent: Mar. 4, 2008

(54) SPRING-LOADED AWL

(75) Inventor: Christopher J. Ryan, West Chester, PA (US)

(73) Assignee: Synthes (U.S.A.), West Chester, PA (US)

( * ) Notice: Subject to any disclaimer, the term of this patent is extended or adjusted under 35 U.S.C. 154(b) by 550 days.

(21) Appl. No.: 10/642,608

(22) Filed: Aug. 19, 2003

(65) Prior Publication Data

US 2005/0043738 A1    Feb. 24, 2005

(51) Int. Cl.
*A61B 17/00* (2006.01)
*A61B 17/32* (2006.01)

(52) U.S. Cl. .................................................. 606/79
(58) Field of Classification Search ................ 606/185, 606/79, 198; 604/164.12, 16, 166.01, 174
See application file for complete search history.

(56) References Cited

U.S. PATENT DOCUMENTS

| 91,806 | A | 6/1869 | Woodbury |
|---|---|---|---|
| 93,937 | A | 8/1869 | Wilcox |
| 430,299 | A | 6/1890 | Rand |
| 787,064 | A | 4/1905 | Welter |
| 824,867 | A | 7/1906 | Houghton |
| 987,355 | A | 3/1911 | Godwin |
| 1,008,226 | A | 11/1911 | Wanlin |
| 1,135,465 | A | 4/1915 | Pollock |
| 1,259,335 | A | 3/1918 | Action |
| 2,338,592 | A | 1/1944 | Lorenzen |
| 2,384,707 | A | 9/1945 | Sweet |
| 2,390,309 | A | 12/1945 | Keys |
| 2,419,045 | A | 4/1947 | Whittaker |
| 2,423,511 | A | 7/1947 | Luben et al. |
| 2,566,738 | A | 9/1951 | Mitchell |
| 2,757,457 | A | 8/1956 | Ziegelski, Sr. |
| 2,795,052 | A | 6/1957 | Felenchak |
| 2,943,389 | A | 7/1960 | DuBois |
| 3,030,959 | A | 4/1962 | Grunert |
| 3,208,452 | A | 9/1965 | Stern |
| 4,007,653 | A | 2/1977 | Cady |
| 4,031,787 | A | 6/1977 | Cady |
| 4,069,586 | A | 1/1978 | Skelton |
| 4,139,011 | A | 2/1979 | Benoit et al. |
| RE29,958 | E | 4/1979 | Cady |
| 4,203,446 | A | 5/1980 | Höffert et al. |
| 4,375,815 | A | 3/1983 | Burns |
| 4,388,925 | A | 6/1983 | Burns |

(Continued)

FOREIGN PATENT DOCUMENTS

DE    19831835 A1    1/2000

(Continued)

*Primary Examiner*—Pedro Philogene
(74) *Attorney, Agent, or Firm*—Stroock & Stroock & Lavan LLP

(57) ABSTRACT

A spring-loaded surgical awl is provided for orthopedic applications that include creating or enlarging holes in bone. The awl has an awl shaft with a cutting tip within a sleeve, with a spring disposed between the awl shaft and sleeve to return the cutting tip of the awl tip to a position within the sleeve after the cutting tip of the awl shaft contacts the bone. The outer sleeve has an end that preferably engages a bone plate and the travel of the awl tip is limited by a shoulder within the outer sleeve.

16 Claims, 6 Drawing Sheets

U.S. PATENT DOCUMENTS

| | | | |
|---|---|---|---|
| 4,449,529 A | | 5/1984 | Burns et al. |
| 4,462,405 A | | 7/1984 | Ehrlich |
| 4,503,856 A | | 3/1985 | Cornell et al. |
| 4,527,561 A | | 7/1985 | Burns |
| 4,535,769 A | | 8/1985 | Burns |
| 4,553,541 A | | 11/1985 | Burns |
| 4,616,649 A | | 10/1986 | Burns |
| 4,624,253 A | | 11/1986 | Burns |
| 4,654,030 A | | 3/1987 | Moll et al. |
| 4,677,979 A | | 7/1987 | Burns |
| 4,931,042 A | | 6/1990 | Holmes et al. |
| 5,030,206 A | | 7/1991 | Lander |
| 5,066,288 A | * | 11/1991 | Deniega et al. ............ 604/274 |
| 5,114,407 A | | 5/1992 | Burbank |
| 5,116,353 A | | 5/1992 | Green |
| 5,152,754 A | | 10/1992 | Plyley et al. |
| 5,215,526 A | | 6/1993 | Deniega et al. |
| 5,217,497 A | | 6/1993 | Mehdian |
| 5,224,952 A | | 7/1993 | Deniega et al. |
| 5,248,298 A | | 9/1993 | Bedi et al. |
| 5,256,147 A | | 10/1993 | Vidal et al. |
| 5,267,965 A | | 12/1993 | Deniega |
| 5,275,583 A | | 1/1994 | Crainich |
| 5,290,243 A | | 3/1994 | Chodorow et al. |
| 5,295,993 A | | 3/1994 | Green |
| 5,312,354 A | | 5/1994 | Allen et al. |
| 5,338,305 A | | 8/1994 | Plyley et al. |
| 5,342,382 A | | 8/1994 | Brinkerhoff et al. |
| 5,350,393 A | | 9/1994 | Yoon |
| 5,351,404 A | | 10/1994 | Smith |
| 5,356,420 A | | 10/1994 | Czernecki et al. |
| 5,360,405 A | * | 11/1994 | Yoon ..................... 604/164.12 |
| 5,387,227 A | | 2/1995 | Grice |
| 5,399,167 A | | 3/1995 | Deniega |
| 5,429,641 A | | 7/1995 | Gotfried |
| 5,431,635 A | | 7/1995 | Yoon |
| 5,437,643 A | | 8/1995 | Transue |
| 5,462,532 A | | 10/1995 | Gresl |
| 5,466,224 A | | 11/1995 | Yoon |
| 5,515,861 A | | 5/1996 | Smith |
| 5,522,831 A | | 6/1996 | Sleister et al. |
| 5,527,335 A | | 6/1996 | Bolduc et al. |
| 5,538,509 A | | 7/1996 | Dunlap et al. |
| 5,549,564 A | | 8/1996 | Yoon |
| 5,569,288 A | | 10/1996 | Yoon |
| 5,569,289 A | | 10/1996 | Yoon |
| 5,569,293 A | | 10/1996 | Yoon |
| 5,571,134 A | | 11/1996 | Yoon |
| 5,573,545 A | | 11/1996 | Yoon |
| 5,575,804 A | | 11/1996 | Yoon |
| 5,578,053 A | | 11/1996 | Yoon |
| 5,584,848 A | | 12/1996 | Yoon |
| 5,584,849 A | | 12/1996 | Yoon |
| 5,586,991 A | | 12/1996 | Yoon |
| 5,591,189 A | | 1/1997 | Yoon |
| 5,591,190 A | * | 1/1997 | Yoon ......................... 606/185 |
| 5,591,193 A | | 1/1997 | Yoon |
| 5,603,719 A | | 2/1997 | Yoon |
| 5,607,439 A | | 3/1997 | Yoon |
| 5,634,934 A | | 6/1997 | Yoon |
| 5,645,076 A | | 7/1997 | Yoon |
| 5,645,556 A | | 7/1997 | Yoon |
| 5,645,557 A | | 7/1997 | Yoon |
| 5,665,102 A | | 9/1997 | Yoon |
| 5,669,885 A | | 9/1997 | Smith |
| 5,676,156 A | | 10/1997 | Yoon |
| 5,676,681 A | | 10/1997 | Yoon |
| 5,676,682 A | | 10/1997 | Yoon |
| 5,676,683 A | | 10/1997 | Yoon |
| 5,688,286 A | | 11/1997 | Yoon |
| 5,697,947 A | | 12/1997 | Wolf et al. |
| 5,730,755 A | | 3/1998 | Yoon |
| 5,741,291 A | | 4/1998 | Yoo |
| 5,746,761 A | | 5/1998 | Turchin |
| 5,772,678 A | | 6/1998 | Thomason et al. |
| 5,807,338 A | | 9/1998 | Smith et al. |
| 5,807,402 A | | 9/1998 | Yoon |
| 5,827,316 A | | 10/1998 | Young et al. |
| 5,882,340 A | * | 3/1999 | Yoon ..................... 604/164.12 |
| 5,941,852 A | | 8/1999 | Dunlap et al. |
| 5,980,493 A | | 11/1999 | Smith et al. |
| 6,019,776 A | | 2/2000 | Preisman et al. |
| 6,080,176 A | | 6/2000 | Young |
| 6,099,544 A | | 8/2000 | Wolf et al. |
| 6,139,550 A | | 10/2000 | Michelson |
| 6,176,867 B1 | | 1/2001 | Wright |
| 6,193,721 B1 | * | 2/2001 | Michelson .................. 606/70 |
| 6,238,407 B1 | * | 5/2001 | Wolf et al. ................. 606/185 |
| 6,248,120 B1 | | 6/2001 | Wyszogrodzki |
| 6,322,574 B1 | | 11/2001 | Lloyd et al. |
| 6,383,186 B1 | | 5/2002 | Michelson |
| 6,398,783 B1 | | 6/2002 | Michelson |
| 6,416,528 B1 | | 7/2002 | Michelson |
| 6,419,661 B1 | | 7/2002 | Kuhr et al. |
| 6,428,542 B1 | | 8/2002 | Michelson |
| 6,454,771 B1 | | 9/2002 | Michelson |
| 6,527,776 B1 | | 3/2003 | Michelson |
| 6,592,586 B1 | | 7/2003 | Michelson |
| 2001/0029387 A1 | | 10/2001 | Wolf et al. |
| 2001/0039387 A1 | | 11/2001 | Rutynowski et al. |
| 2002/0026207 A1 | | 2/2002 | Stellon et al. |
| 2002/0045896 A1 | | 4/2002 | Michelson |
| 2002/0148129 A1 | | 10/2002 | Donnellan |
| 2003/0018335 A1 | | 1/2003 | Michelson |
| 2003/0040752 A1 | | 2/2003 | Kitchens |
| 2003/0045834 A1 | | 3/2003 | Wing et al. |
| 2003/0045880 A1 | | 3/2003 | Michelson |
| 2003/0069595 A1 | | 4/2003 | Phung et al. |

FOREIGN PATENT DOCUMENTS

| | | |
|---|---|---|
| EP | 0350291 A2 | 1/1990 |
| EP | 0495633 A1 | 7/1992 |
| EP | 0499457 A1 | 8/1992 |
| EP | 0535974 A1 | 4/1993 |
| EP | 0350291 B1 | 9/1994 |
| EP | 0499457 B1 | 5/1997 |
| EP | 0873720 A1 | 10/1998 |
| JP | 402065854 A | 3/1990 |
| JP | 404317646 A | 11/1992 |
| JP | 405092011 A | 4/1993 |
| JP | 405168644 A | 7/1993 |
| JP | 405200041 A | 8/1993 |
| JP | 407047076 A | 2/1995 |
| JP | A-H07-51280 | 2/1995 |
| JP | 407143992 A | 6/1995 |
| WO | WO9918865 A1 | 4/1999 |

* cited by examiner

SPRING-LOADED AWL

FIELD OF THE INVENTION

The present invention relates generally to an awl for use in orthopedic surgery, and more particularly to an awl having a cutting tip that is used to create or enlarge holes in bone.

BACKGROUND OF THE INVENTION

The present invention relates generally to an awl for use in orthopedic surgery. Awls generally in orthopedic surgery are used to create or enlarge holes in bone. Although a drill may be used to create a hole in bone for orthopedic surgery, the precision required in aligning holes, for example, for vertebral surgery, requires the use of a drill guide along with the drill. Rather than using two devices, the present invention allows a surgeon to use a single device to create a properly aligned hole. An awl may also be used for creating starter holes for self-drilling screws, although it is not limited to such uses.

SUMMARY OF THE INVENTION

The present invention relates to an awl used in orthopedic surgery. The awl of the present invention in one embodiment has a shaft with a cutting tip, a spring, a bottom outer sleeve, a top outer sleeve, an inner sleeve, and a hand grip. More particularly the cutting tip of the awl of this embodiment is normally maintained within an outer sleeve by a spring which provides a biasing force. In one embodiment, the awl may have a distal end which engages a bone plate, and a proximal end, which may have a hand grip for operating the awl. Preferably, the awl engages the bone plate with the awl being oriented to match the desired trajectory of the bone fasteners, such as for example screws, through the bone plate. The awl preferably engages the bone plate in a releasable manner. Applying pressure to the hand grip in a direction toward the distal end of the awl pushes the shaft of the awl against the spring which causes the cutting tip of the awl to leave the outer sleeve and contact the bone surface. Depending upon the pressure applied and the distance traveled by the shaft, the cutting tip preferably pierces the bone, with travel of the cutting tip preferably limited by a shoulder within the outer sleeve. Releasing pressure on the hand grip allows the biasing force of the spring to return the cutting tip of the awl to a position within the outer sleeve. The distal end of the spring rests on a shoulder inside the inner sleeve and the proximal end of the spring rests on a shoulder formed by the junction of the inner sleeve and the awl shaft. The outer sleeve may include slots that allow the tool to be cleaned and sterilized between surgeries.

The awl of the present invention in another embodiment comprises a shaft with a cutting edge formed on one end, an outer sleeve, and a biasing member configured to bias the shaft to an initial position within the outer sleeve. The shaft is surrounded by the outer sleeve and movable in the axial direction with respect to the outer sleeve by a predetermined distance to limit the depth of penetration of the cutting tip into a bone. The elastic member may be a coil spring, which may surround the shaft. Preferably, one end of the outer sleeve has a means, preferably a threaded connection, of releasably attaching to a bone plate. The threads at the end of the outer sleeve may be conical. Preferably, the initial position of the shaft is such that the cutting edge of the shaft is surrounded by the outer sleeve. There may be one or more slots, or openings of another shape, through the outer sleeve. The awl apparatus may further comprise a handle attached to the end of the shaft.

A method of installing a bone plate to a bone surface is also described, the method comprising the steps of (a) contacting the bone plate to the bone surface; (b) contacting an awl apparatus to a first fastener hole in a bone plate, the awl apparatus comprising a shaft having a cutting edge formed on a distal end, an outer sleeve within which the shaft is axially movable, and a biasing member configured to bias the shaft to an initial position within the outer sleeve; (c) creating a hole in the bone by applying axial pressure to the distal end of the shaft; (d) removing the awl apparatus from the bone plate while holding the bone plate in contact with the bone surface; and (e) installing a bone anchor through the first fastener hole into the hole created in step (c). The awl may then be attached to a second fastener hole in the bone plate and steps (b) through (e) repeated for the second fastener hole. The awl may be attached to the bone plate prior to contacting the bone plate to the bone surface. Preferably, the awl is attached to the bone plate by threading.

BRIEF DESCRIPTION OF THE DRAWINGS

While preferred features of the present invention are disclosed in the accompanying drawings, the invention is not limited to such preferred features wherein.

DETAILED DESCRIPTION OF THE PREFERRED EMBODIMENT

Figure 1:
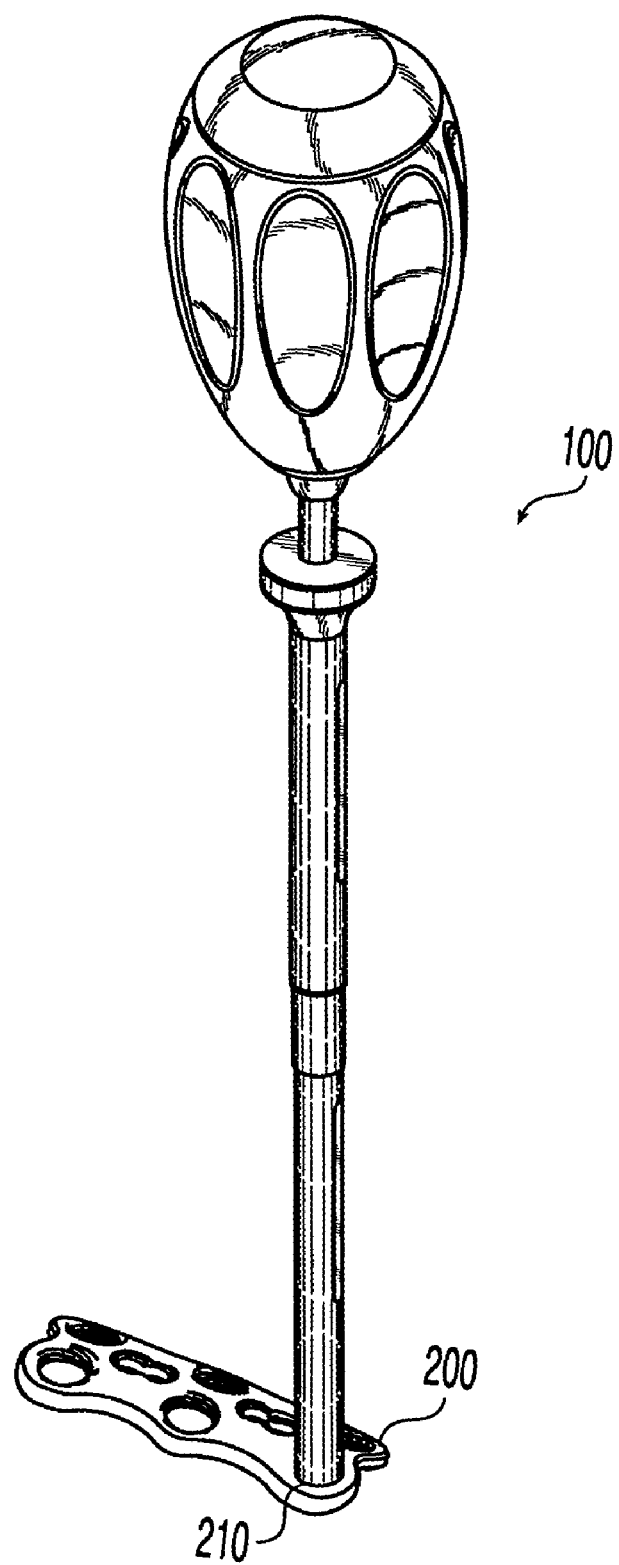
FIG. 1 is a perspective view of the awl attached to a bone plate.
Figure 2:
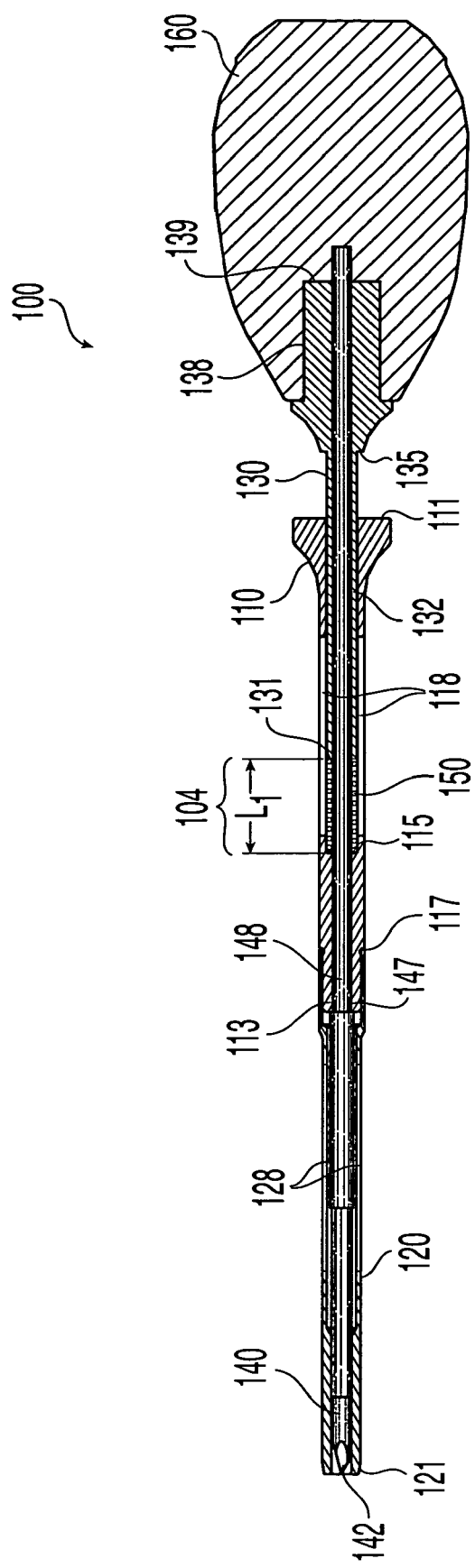
FIG. 2 is a cross-sectional view of the awl of FIG. 1.

Referring to FIG. 1, there is shown an exemplary spring-loaded awl assembly 100, engaging an anchor hole 210 of a cervical bone plate 200. Awl assembly 100 is used for orthopedic applications that include creating or enlarging holes in bone. While the spring-loaded awl assembly 100 is shown and described as used with a cervical plate 200 for use in the cervical region of the spine, it will be appreciated that the spring-loaded awl assembly 100 can be used with other bone plates. As shown in FIG. 2, assembly 100 includes a top outer sleeve 110, a bottom outer sleeve 120, an inner sleeve 130, an awl shaft 140, a spring 150, and a hand grip 160. All components may be fabricated from a biocompatible material such as stainless steel. Hand grip 160 may be fabricated from plastic or rubber, preferably silicone rubber to allow assembly 100 to be subjected to high temperatures for sterilization, for comfort, to reduce weight, and for ease of fabrication. Applying pressure to hand grip 160 against the biasing force of spring 150 causes the cutting tip 142 of awl shaft 140 to exit the distal end 122 of the bottom outer sleeve 120, allowing cutting tip 142 during its intended use to contact and preferably pierce bone when, for example, the assembly is engaged with a bone plate in contact with bone.

Figure 3:
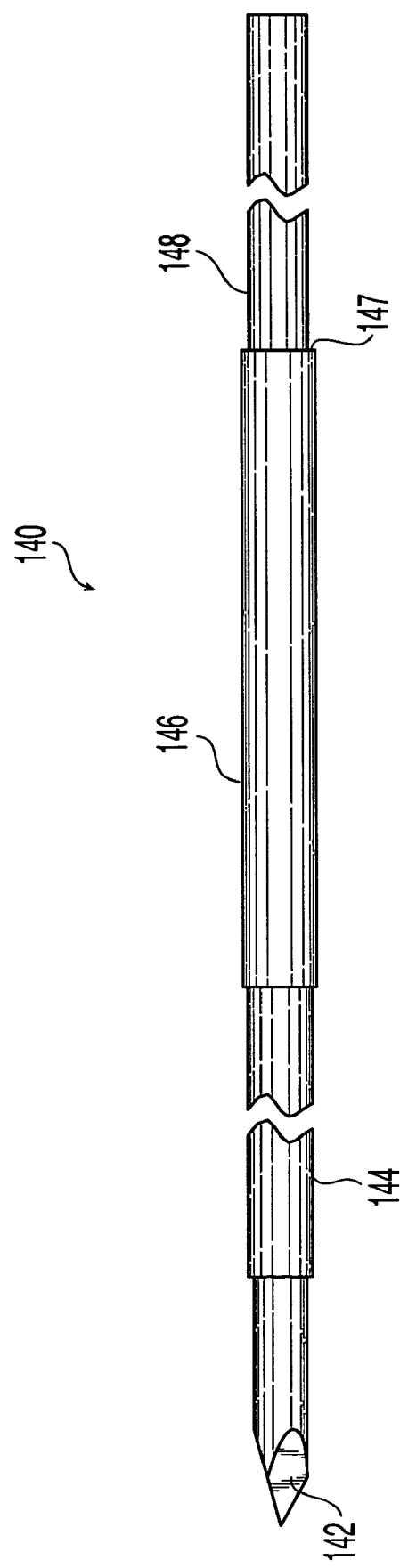
FIG. 3 is a side view of the awl shaft.

With reference to FIG. 3, awl shaft 140 is approximately 200 mm long and has a cutting tip 142, a distal portion 144, a medial portion 146, and a proximal portion 148, exemplary diameters of which are about 2.5 mm, about 3.0 mm, about 3.5 mm, and about 2.8 mm, respectively. Other dimensions for the diameter of the cutting tip, distal portion, medial portion, and proximal portion may also be used, and the length of shaft 140 may also be varied. The junction of medial section 146 and proximal section 148 of awl shaft 140 may form a shoulder 147.

Figure 4:
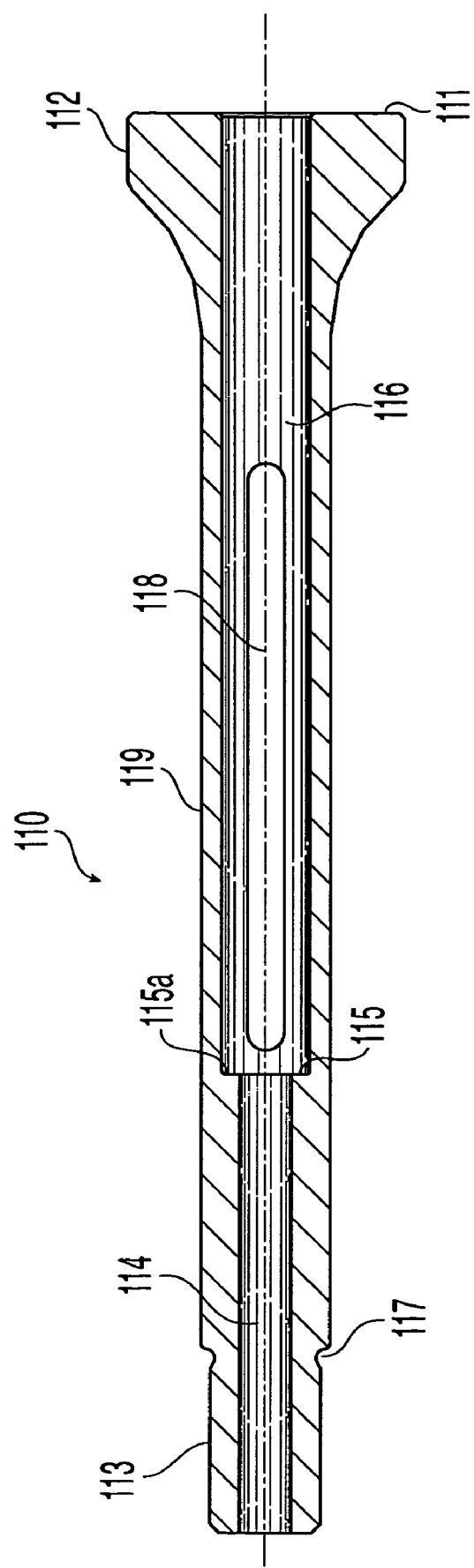
FIG. 4 is a side view of the top outer sleeve.

With reference to FIG. 4, top outer sleeve 110 has a flared section 112 at its proximal end, and has a throughbore 114 with an exemplary diameter of about 2.85 mm and a counterbored section 116 with an exemplary diameter of about 4.78 mm. Other dimensions for the diameters of through bore 114 and counterbore for counterbored section 116 may be used. Distal end 115 of counterbored section 116 forms a shoulder 115*a*. Top outer sleeve has a length of approximately 80 mm, and shoulder 115*a* is about 25 mm from distal end 113 of top outer sleeve 110. Shoulder 115*a* may be formed at different lengths. Diametrically opposed slots 118 through the wall 119 of top outer sleeve 110 are approximately 2 mm wide and approximately 30 mm long, and facilitate cleaning and sterilizing awl assembly 100 between surgeries. Other dimensions and shapes of openings may be used instead of the slots 118 described. One or more slots 118 may be provided and the slots 118 can have the same or different dimensions. The distal end 113 of top outer sleeve 110 has an exemplary outer diameter of about 6 mm to allow it to be inserted into proximal section 126 of bottom outer sleeve 120. Distal end 113 of top outer sleeve 110 may be externally threaded to facilitate releasably joining distal end 113 of top outer sleeve 110 to bottom outer sleeve 120. Providing a releasable connection between top outer sleeve 110 and bottom outer sleeve 120 may allow the top and bottom outer sleeves 110, 120 to be disconnected to facilitate cleaning and sterilizing. Alternatively, top and bottom outer sleeves 110, 120 may be joined by, for example, rolling, welding, brazing, etc. Distal end 113 of top outer sleeve 110 may include a groove 117 to facilitate joining top and bottom outer sleeves 110, 120.

Figure 5:
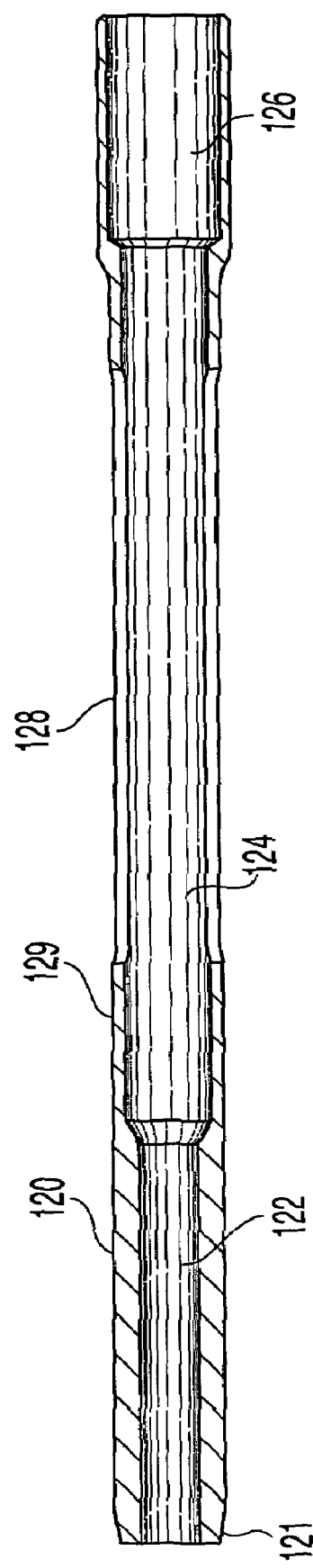
FIG. 5 is a side view of the bottom outer sleeve.

With reference to FIG. 5, bottom outer sleeve 120 has a throughbore 122 with an exemplary diameter of about 3.1 mm. The inside diameter of the bore increases to approximately 4.55 mm in intermediate section 124 and to approximately 6 mm in proximal section 126. Bottom outer sleeve 120 has a length of approximately 80 mm and proximal section 126 is approximately 12 mm long. The outside diameter of proximal section 126 is approximately 7 mm, with the remainder of bottom outer sleeve 120 having an outside diameter of approximately 5.85 mm. Diametrically opposed slots 128 through wall 129 of bottom outer sleeve are approximately 2 mm wide and about 30 mm long, and facilitate cleaning and sterilizing awl assembly 100 between surgeries. Other dimensions, shapes, locations, and number of slots 128 may be provided. Distal end 121 of bottom outer sleeve 120 may be threaded for mechanical attachment to the perimeter of anchor hole 210 of bone plate 200, although other methods of releasably attaching awl assembly 100 to bone plate 200 are possible. In some cases, assembly 100 will be used with bone plates with conical fastener holes and distal end 121 of bottom outer sleeve 120 will then have an external conical thread to match the fastener holes.

Figure 6:
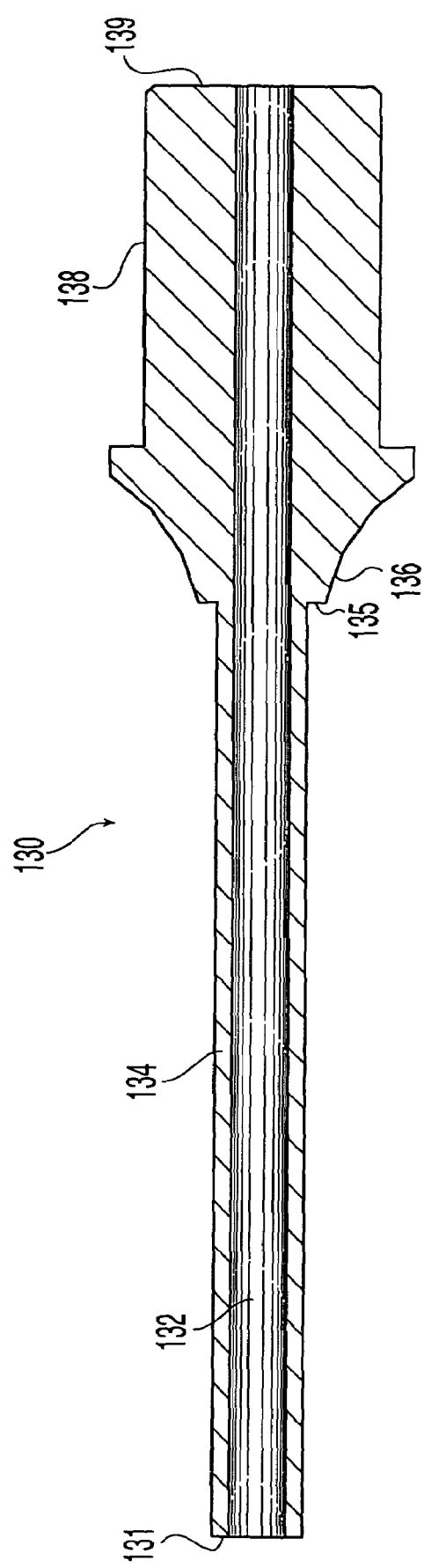
FIG. 6 is a side view of the top outer sleeve.

With reference to FIG. 6, inner sleeve 130 has a throughbore 132 with an exemplary diameter of about 2.85 mm, a distal portion 134 with an exemplary outside diameter of 6.5 mm and a distal face 131, a flared medial section 136 with an exemplary maximum outside diameter of about 15.5 mm, and a proximal portion 138 approximately 15 mm long and 12 mm in diameter, with proximal face 139.

Referring again to FIG. 2, assembly of awl assembly 100 will now be explained. Proximal portion 148 of awl shaft 140 is inserted into distal end 121 of bottom outer sleeve 120 until shoulder 147 of awl shaft 140 rests against distal end 113 of top outer sleeve 110. Spring 150 is placed over proximal portion 148 of awl shaft 140 and proximal end 148 of awl shaft 140 is inserted into throughbore 132 of inner sleeve 130, with inner sleeve located on awl shaft 140 in such a position that the gap 104 between shoulder 115*a* of top outer sleeve 110 and distal face 131 of inner sleeve 130 (dimension $L_1$; exemplary dimension of about 17 mm) is slightly less than the free length of spring 150. The travel of the cutting tip 142 of awl shaft (and consequently the depth of hole bored) is changed by varying dimension $L_1$ and the length of spring 150. It will be appreciated that the spring could be in a location other than around the proximal portion 148 of awl shaft 140. In addition, an elastic member other than a coil spring could serve the same function as spring 150. Inner sleeve 130 is mechanically joined to proximal end 148 of awl shaft 140, preferably by welding or brazing the interface of proximal face 139 of inner sleeve 130 and proximal portion 148 of awl shaft 140. Bottom outer sleeve 110 is slipped over awl shaft 140 and distal end 113 of top outer shaft 110, and top and bottom outer sleeves 110, 120 are mechanically joined, preferably by laser welding. However, other means of mechanically joining top and bottom outer sleeves 110, 120, including threaded connections, brazing, or rolling, are possible. In addition, the outer sleeve can be a single piece. Awl shaft 140 is preferably free to rotate within outer sleeves 110, 120 to facilitate clearing bone debris from the path of cutting tip 142 as the depth of the hole being created increases. Handle grip 160 preferably is attached to proximal portion 138 of inner sleeve 130, preferably by molding the handle onto proximal portion 138 of inner sleeve 130, or by bonding or gluing.

Use of the awl assembly 100 to create a hole in bone will now be described. Referring to FIGS. 1 and 2, awl assembly 100 is releasably attached, preferably by a threaded connection, to anchor hole 210 of bone plate 200. Other methods of releasably attaching awl assembly to anchor hole 210 of bone plate 200 are possible, such as an expanding ferrule or ball detents. Assembly 100 may be used as a plate holder when applying plate 200 to the bone surface. Applying pressure in the axial direction to hand grip 160 toward the bone plate results in the subassembly of handle grip 160, inner sleeve 130, and awl shaft 140 traveling in the distal direction; and cutting tip 142 of awl shaft 140 making contact with bone. Travel of the subassembly of handle grip 160, inner sleeve 130, and awl shaft 140 in the distal direction is limited by shoulder 135 of inner sleeve 130 contacting proximal face 111 of top outer sleeve 110. This travel limit in turn limits the depth of hole formed by awl assembly 100. Releasing pressure on handle grip 160 results in the subassembly of handle grip 160, inner sleeve 130, and awl shaft 140 returning to its original position in which shoulder 147 of awl shaft 140 rests against distal end 113 of top outer sleeve 110, the contact between shoulder 147 and distal end 113 limiting travel of the subassembly of handle grip 160, inner sleeve 130, and awl shaft 140 in the proximal direction. Hand grip 160 may be rotated as axial pressure is applied to facilitate the clearing of debris from the path of cutting tip 142.

After the initial hole is created in the bone by awl assembly 100, plate 200 is held in place either by another plate holder (e.g., a rod in another threaded hole of plate 200), or by a surgeon's or nurse's finger. A bone screw is then inserted through anchor hole 210 and the awl is attached to another anchor hole to drill another hole.

While various descriptions of the present invention are described above, it should be understood that the various features can be used alone or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

The invention claimed is:

1. An awl apparatus for penetrating bone, comprising:
   a shaft having a proximal end and a distal end, with a cutting edge formed on the distal end;
   an outer sleeve having a wall, a proximal end, and a distal end, wherein the outer sleeve surrounds at least a portion of the shaft and is movable with respect to the shaft, the outer sleeve including a plurality of openings to facilitate cleaning and sterilization of the awl;
   an inner sleeve having a proximal end and a distal end, wherein at least a portion of the inner sleeve is located in between the shaft and the outer sleeve; and
   a biasing member configured to bias the shaft to an initial position within the outer sleeve, wherein the biasing member surrounds at least a portion of the shaft and is located in between the outer sleeve and the distal end of the inner sleeve;
   wherein the shaft is movable in the axial direction with respect to the outer sleeve by a predetermined distance to limit the depth of penetration of the cutting tip into a bone; and
   wherein the shaft can be rotated within the outer sleeve to aid in penetrating a bone.

2. The awl apparatus of claim 1, wherein the biasing member is a coil spring.

3. The awl apparatus of claim 1, wherein the biasing member is a coil spring surrounding the shaft.

4. The awl apparatus of claim 1, wherein the distal end of the outer sleeve has external threads for releasable attachment to a bone plate.

5. The awl apparatus of claim 1, wherein the initial position of the shaft is such that the cutting edge of the shaft is surrounded by the outer sleeve.

6. The awl apparatus of claim 1, wherein the distal end of the outer sleeve is conically tapered for releasable attachment to a bone plate.

7. The awl apparatus of claim 1, further comprising a shoulder for limiting depth of penetration into the bone by the cutting edge.

8. The awl apparatus of claim 1, further comprising a handle attached to the end of the shaft.

9. An awl assembly comprising:
   a top outer sleeve having a distal end, a proximal end, and a throughbore extending from said distal end to said proximal end, wherein the top outer sleeve includes a plurality of openings to facilitate cleaning and sterilization of the awl;
   a bottom outer sleeve having a distal end, a proximal end, and a throughbore extending from said distal end to said proximal end, wherein said proximal end of said bottom outer sleeve is sized and configured to releasably engage said top outer sleeve, wherein the bottom outer sleeve includes a plurality of openings to facilitate cleaning and sterilization of the awl;
   an inner sleeve having a distal end, a proximal end, and a throughbore extending from said distal end to said proximal end, wherein said inner sleeve is sized and configured to be at least partially received within the throughbore of the top outer sleeve;
   an awl shaft having a cutting tip formed on a distal end thereof, wherein said awl shaft is sized and configured to be slideably disposed within the throughbore of the inner sleeve, the throughbore of the top outer sleeve and the throughbore of the bottom outer sleeve; and
   a spring element, the spring element providing a biasing force for maintaining the cutting tip within the bottom outer sleeve, wherein the spring element surrounds at least a portion of the shaft and is located in between the top outer sleeve and the distal end of the inner sleeve;
   wherein the distal end of the bottom outer sleeve is sized and configured to releasably engage an anchor hole of a bone plate.

10. The awl assembly of claim 9, wherein the throughbore of the top outer sleeve includes a shoulder formed therein, the spring element being located in between the shoulder and the distal end of the inner sleeve.

11. The awl assembly of claim 9, wherein the proximal end of the awl shaft includes a hand grip connected thereto.

12. The awl assembly of claim 9, wherein the distal end of the top outer sleeve is disposed within the proximal end of the bottom outer sleeve.

13. The awl assembly of claim 9, wherein said distal end of said top outer sleeve is threaded for threadedly engaging the bottom outer sleeve.

14. The awl assembly of claim 9, wherein the distal end of the bottom outer sleeve is externally threaded for threadedly engaging internal threads formed in the anchor hole of the bone plate.

15. The awl assembly of claim 9, wherein the inner sleeve is mechanically joined to the proximal end of the awl shaft.

16. The awl assembly of claim 9, wherein the awl shaft is free to rotate within the top outer sleeve and the bottom outer sleeve.

* * * * *